United States Patent
Nakama et al.

(10) Patent No.: US 10,330,651 B2
(45) Date of Patent: Jun. 25, 2019

(54) THERMAL CONDUCTIVITY DETECTOR AND GAS CHROMATOGRAPH

(71) Applicant: SHIMADZU CORPORATION, Kyoto-shi, Kyoto (JP)

(72) Inventors: Yuji Nakama, Yamatokoriyama (JP); Shigeaki Shibamoto, Kyoro (JP); Kazunori Takahashi, Kyoutanabe (JP); Minoru Kashihara, Joyo (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 64 days.

(21) Appl. No.: 14/870,208

(22) Filed: Sep. 30, 2015

(65) Prior Publication Data
US 2016/0103105 A1 Apr. 14, 2016

(30) Foreign Application Priority Data

Oct. 10, 2014 (JP) .................... 2014-209484

(51) Int. Cl.
*G01N 25/18* (2006.01)
*G01N 30/62* (2006.01)
*G01N 30/66* (2006.01)

(52) U.S. Cl.
CPC ............ *G01N 30/62* (2013.01); *G01N 25/18* (2013.01); *G01N 30/66* (2013.01)

(58) Field of Classification Search
CPC ........ G01N 30/62; G01N 25/18; G01N 30/66; G01N 2030/025
See application file for complete search history.

(56) References Cited

U.S. PATENT DOCUMENTS 4,185,490 A * 1/1980 Clouser .................. G01N 27/18
73/23.35
4,254,654 A 3/1981 Clouser et al.
(Continued)

FOREIGN PATENT DOCUMENTS

CN 1685224 A 10/2005
EP 0344639 A2 12/1989
(Continued)

OTHER PUBLICATIONS

Office Action dated Dec. 5, 2016, issued in counterpart Chinese Patent Application No. 201510566584.3, with English translation. (10 pages).

(Continued)

*Primary Examiner* — Justin Seo
*Assistant Examiner* — John M Royston
(74) *Attorney, Agent, or Firm* — Westerman, Hattori, Daniels & Adrian, LLP (57) ABSTRACT

A thermal conductivity detector that causes a fluid to come into contact with the surface of a heated temperature sensing element, that causes the temperature of the temperature sensing element to change according to the thermal conductivity of the fluid, and that detects the fluid based on a change in the electrical resistance of the temperature sensing element at that time or on a change in the value of a current to be applied to the temperature sensing element is provided. The thermal conductivity detector includes a cell space where the temperature sensing element is accommodated and to which a fluid is introduced and from which the fluid is discharged, a buffer space that is connected to a fluid outlet of the cell space, and a discharge channel that is connected to a fluid outlet of the buffer space.

4 Claims, 7 Drawing Sheets

(56) References Cited

U.S. PATENT DOCUMENTS

| | | | |
|---|---|---|---|
| 4,856,319 A | 8/1989 | Golay | |
| 2004/0250601 A1 | 12/2004 | Lin | |
| 2006/0236751 A1* | 10/2006 | Lin | G01N 30/66 73/23.4 |
| 2008/0014652 A1* | 1/2008 | Caprai | G01N 30/32 436/161 |
| 2010/0242573 A1* | 9/2010 | Matsuhama | G01N 25/18 73/25.03 |

FOREIGN PATENT DOCUMENTS

| | | |
|---|---|---|
| EP | 0 713 098 A2 | 5/1996 |
| JP | 2-27257 A | 1/1990 |
| JP | 02-27257 A | 1/1990 |
| JP | 07-043356 A | 2/1995 |
| JP | 2010-230591 A | 10/2010 |

OTHER PUBLICATIONS

Office Action dated Feb. 20, 2018, issued in counterpart Japanese Application No. 2014-209484, with English machine translation. (5 pages).
Office Action dated Aug. 28, 2018, isssued in counterpart Japanese Application No. 2014-209484, with English translation (6 pages).

* cited by examiner

THERMAL CONDUCTIVITY DETECTOR AND GAS CHROMATOGRAPH

BACKGROUND OF THE INVENTION

1. Field of the Invention

The present invention relates to a thermal conductivity detector used in gas chromatography (GC), and a gas chromatograph.

2. Description of the Related Art

As a detector used in gas chromatography, a thermal conductivity detector (TCD) is known (for example, see JP 07-043356 A (reference document 1), U.S. Pat. No. 4,254,654 (reference document 2)). A thermal conductivity detector uses exchange of heat between a heating element (filament) and a fluid (gas) flowing around the heating element. Gas is introduced into a space where the heating element is accommodated, and is then discharged from the space.

The thermal conductivity detector is provided with at least two cell spaces where a filament element is arranged. The filament element is arranged in each cell space.

Reference gas flows through one of the cell spaces. Carrier gas flows through the other cell space, and sample gas which is an analysis target is thus introduced. Then, electrical output of the two filament elements is input to a detection circuit. At the detection circuit, a correction current according to the difference in the thermal conductivity caused by introduction of the sample gas flows. The thermal conductivity detector detects this correction current to thereby detect a sample.

SUMMARY OF THE INVENTION

As described in the reference document 1, a conventional thermal conductivity detector is provided with a tube (discharge tube) for discharging sample gas and reference gas. The discharge tube is communicated with the atmosphere, and a change in the atmospheric pressure is transmitted to gas flowing around the filament element. This changes the flow velocity of the gas, and the amount of heat that is removed from the filament by forced convection is changed. When the amount of heat that is removed from the filament changes, the temperature of the filament changes, and thus, the resistance value of the filament changes.

In the reference document 1, two filaments are used, and there is a machine difference between the filaments. Accordingly, the change in the resistance value is not completely the same for the two filaments. Thus, when the atmospheric pressure changes, the balance of a bridge circuit used as the detection circuit is upset. As a result, there is a problem that the output of the thermal conductivity detector swings, and the baseline is changed.

The thermal conductivity detector described in the reference document 2 switches between sample gas and reference gas at a cycle of 100 msec and introduces the gas to the filament to thereby obtain signals of the sample gas and the reference gas by one filament. This thermal conductivity detector removes a change in the baseline due to a change in the temperature or a change in the atmospheric pressure by taking a difference. However, there is a problem that a change in the atmospheric pressure less than 100 msec cannot be removed, and that the baseline is changed.

A change in the baseline that is based on a change in the atmospheric pressure causes reduction in the minimum amount of detection or a distortion in the chromatogram, and thus leads to a problem especially in a highly sensitive analysis. Accordingly, there is a need to remove the change in the baseline that is based on a change in the atmospheric pressure.

The object of the present invention is to suppress a change in the baseline, of the thermal conductivity detector, that is based on a change in the atmospheric pressure.

A thermal conductivity detector of an embodiment of the present invention is a thermal conductivity detector that causes a fluid to come into contact with the surface of a heated temperature sensing element, that causes the temperature of the temperature sensing element to change according to the thermal conductivity of the fluid, and that detects the fluid based on a change in the electrical resistance of the temperature sensing element at that time or on a change in the value of a current to be applied to the temperature sensing element, and includes a cell space where the temperature sensing element is accommodated and to which a fluid is introduced and from which the fluid is discharged, a buffer space that is connected to a fluid outlet of the cell space, and a discharge channel that is connected to a fluid outlet of the buffer space.

A gas chromatograph of an embodiment of the present invention is a gas chromatograph for supplying carrier gas to a column through a sample introduction section, and detecting by a detector, a gas component that has been separated by and that has flowed out from the column, the gas chromatograph including the thermal conductivity detector of the embodiment of the present invention as the detector.

The thermal conductivity detector of the embodiment of the present invention and the gas chromatograph of the embodiment of the present invention are capable of suppressing a change in a baseline of the thermal conductivity detector that is based on a change in the atmospheric pressure.

DETAILED DESCRIPTION OF THE PREFERRED EMBODIMENTS

A thermal conductivity detector of an embodiment of the present invention is, for example, provided with a cell member for forming the cell space, a buffer space member for forming the buffer space, a discharge channel member for forming the discharge channel, and a connection tube for connecting the cell member and the buffer space member. However, the configuration of the thermal conductivity detector of the embodiment of the present invention is not limited thereto.

Figure 1:
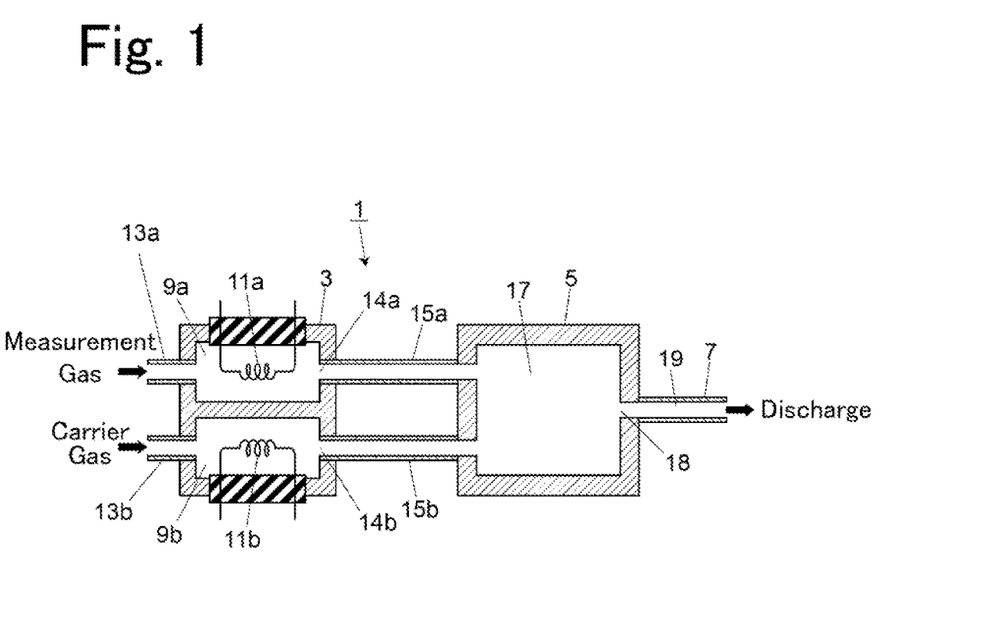
FIG. 1 is a schematic cross-sectional diagram showing an embodiment of a thermal conductivity detector.
Figure 2:
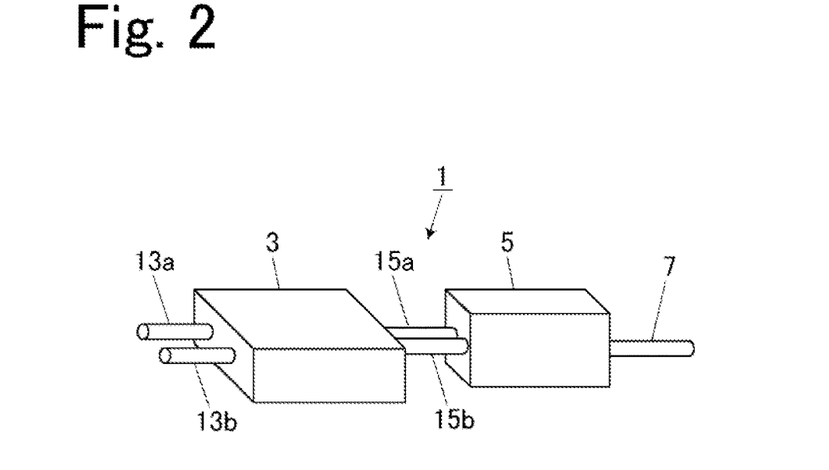
FIG. 2 is a schematic perspective diagram of an external appearance of the embodiment.
Figure 3:
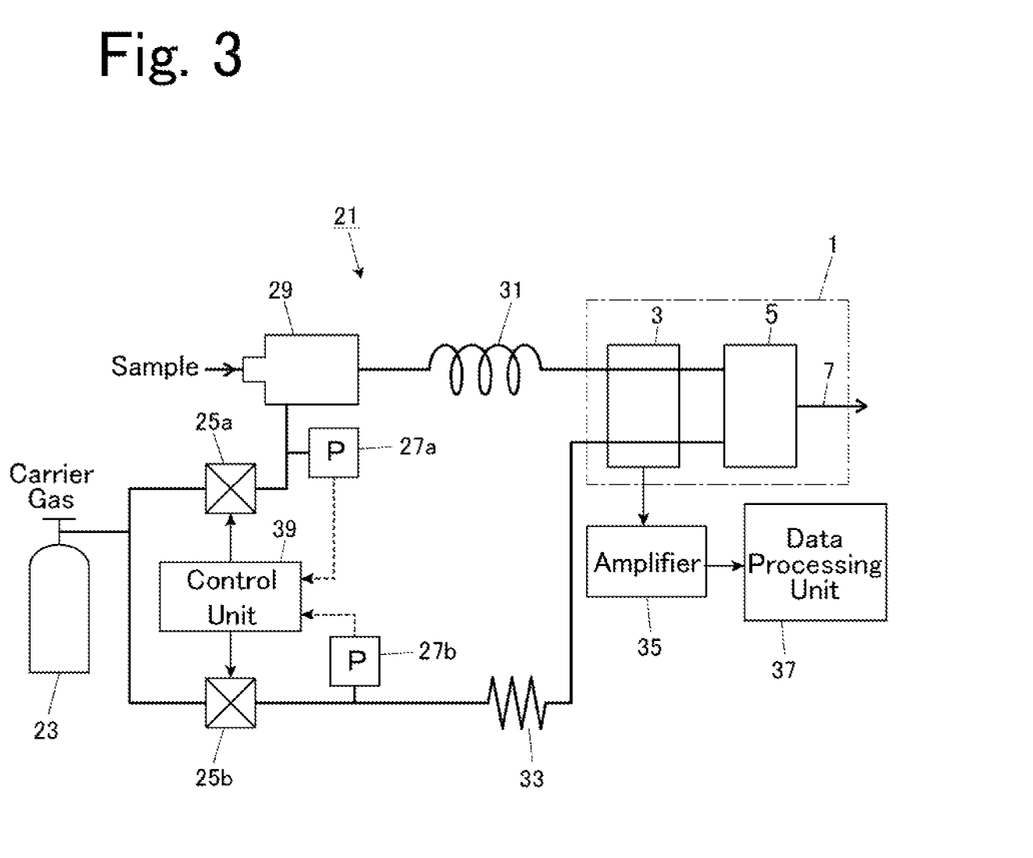
FIG. 3 is a schematic configuration diagram for describing an embodiment of a gas chromatograph.

FIG. 1 is a schematic cross-sectional diagram for describing an embodiment of the thermal conductivity detector. FIG. 2 is a schematic configuration diagram for describing the embodiment. FIG. 3 is a schematic configuration diagram for describing an embodiment of a gas chromatograph. First, an embodiment of a gas chromatograph is described with reference to FIG. 3.

Regarding a gas chromatograph 21, carrier gas, such as He, is supplied from a gas supply source 23 by being branched to a reference-side channel and a sample-side channel. A flow control valve 25a, a pressure sensor 27a, a sample vaporizing chamber 29 (sample introduction section), and a column 31 are provided on the sample-side channel. Carrier gas is sent into the column 31 through the sample vaporizing chamber 29. The sample vaporizing chamber 29 is heated to a high temperature, and when a liquid sample is injected, it is instantly vaporized, and is sent to the column 31 by the flow of the carrier gas. Measurement gas (mixed gas of carrier gas and a sample) which has passed through the column 31 passes through a sample-side cell space provided to a metal block 3 of a thermal conductivity detector 1, and is then discharged to the atmosphere through a buffer 5 and a resistance tube 7.

A flow control valve 25b, a pressure sensor 27b, and a resistor 33 are provided on the reference-side channel. The resistor 33 is, for example, a throttle valve, for example. Carrier gas which has passed through the resistor 33 passes through a reference-side cell space provided to the metal block 3 of the thermal conductivity detector 1, and is then discharged to the atmosphere through the buffer 5 and the resistance tube 7.

A signal detected at the thermal conductivity detector 1 is input to a data processing unit 37 via an amplifier 35. The data processing unit 37 generates a chromatogram.

A control unit 39 monitors gas pressures of the channels by the respective pressure sensors 27a and 27b. The control unit 39 controls the flow control valves 25a and 25b so that the gas pressures of the respective channels are at predetermined values. Carrier gas thus flows through the sample-side channel and the reference-side channel at predetermined flow rates.

The thermal conductivity detector 1 will be described with reference to FIGS. 1 and 2.

The thermal conductivity detector 1 includes the metal block 3 (cell member), the buffer 5 (buffer space member), and the resistance tube 7 (discharge channel member).

A sample-side cell space 9a and a reference-side cell space 9b that are separated from each other are formed inside the metal block 3. The metal block 3 is made of stainless steel, for example. A filament 11a (temperature sensing element) is accommodated in the sample-side cell space 9a. A filament 11b (temperature sensing element) is accommodated in the reference-side cell space 9b. The filaments 11a and 11b are made of metal such as tungsten. The filaments 11a and 11b are heated by being supplied with current from outside.

One end portions of metal tubes 13a, 13b, 15a, and 15b, for example, are fitted into the sample-side cell space 9a and the reference-side cell space 9b of the metal block 3, for example. The tube 13a introduces measurement gas into the sample-side cell space 9a from a fluid inlet of the sample-side cell space 9a. The tube 15a (connection tube) discharges measurement gas from a fluid outlet 14a of the sample-side cell space 9a. The tube 13b introduces carrier gas into the reference-side cell space 9b from a fluid inlet of the reference-side cell space 9b. The tube 15b (connection tube) discharges measurement gas from a fluid outlet 14b of the reference-side cell space 9b. The tubes 13a, 13b, 15a, and 15b are welded and integrated with the metal block 3, for example.

Measurement gas which has passed through the column 31 (see FIG. 3) is introduced into the sample-side cell space 9a through the tube 13a. Only the carrier gas is introduced into the reference-side cell space 9b through the tube 13b as comparison gas.

The other end portion of each of the tubes 15a and 15b, that is, the end portion on the opposite side from the metal block 3, is connected to, for example, the buffer 5 by a connector (not shown).

A buffer space 17 is formed inside the buffer 5. The buffer space 17 is connected to the fluid outlet 14a of the sample-side cell space 9a and the fluid outlet 14b of the reference-side cell space 9b through the tubes 15a and 15b. The buffer 5 is, for example, a metal tank whose inner diameter is 100 mm and whose length is 440 mm. The cross-sectional area of the buffer space 17 is greater than the cross-sectional areas of the tubes 15a and 15b and the cross-sectional area of the resistance tube 7.

One end of the resistance tube 7 is connected to the buffer 5 by, for example, a connector (not shown). A discharge channel 19 inside the resistance tube 7 is connected to a fluid outlet 18 of the buffer space 17.

When a sample component is not included in measurement gas, heat is removed from the sample-side filament 11a at a constant rate by thermal conduction through carrier gas. The sample-side filament 11a is balanced at a temperature at which the amount of heat that is supplied by heating and the amount of heat that is released are equal, and has electrical resistance according to the temperature. When a sample component is included in measurement gas, the thermal conductivity of the measurement gas is changed according to the component, and the amount of heat that is released from the sample-side filament 11a is changed, and thus, the temperature of the sample-side filament 11a, that is, the electrical resistance, is changed.

Figure 4:
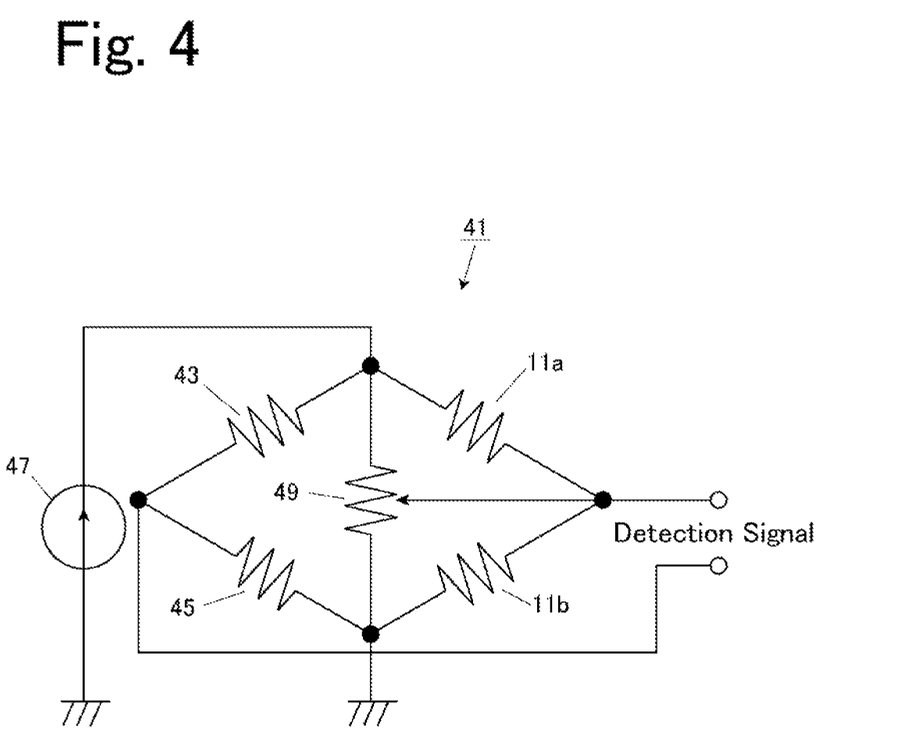
FIG. 4 is a schematic circuit diagram illustrating a Wheatstone bridge circuit as a detection circuit for obtaining a detection signal of the thermal conductivity detector.

This change in resistance is detected by a Wheatstone bridge circuit 41 as a detection circuit as shown in FIG. 4, for example. The bridge circuit 41 is formed by including the sample-side filament 11a, the reference-side filament 11b, and two fixed resistors 43 and 45 having the same resistance value. A constant current is supplied to the bridge circuit 41 by a constant current source 47. A variable resistor 49 is provided at a diagonal position of the bridge circuit 41. The bridge circuit 41 is enabled to adjust a detection signal to zero by adjusting the variable resistor 49. This detection signal is supplied to the amplifier 35.

Figure 5:
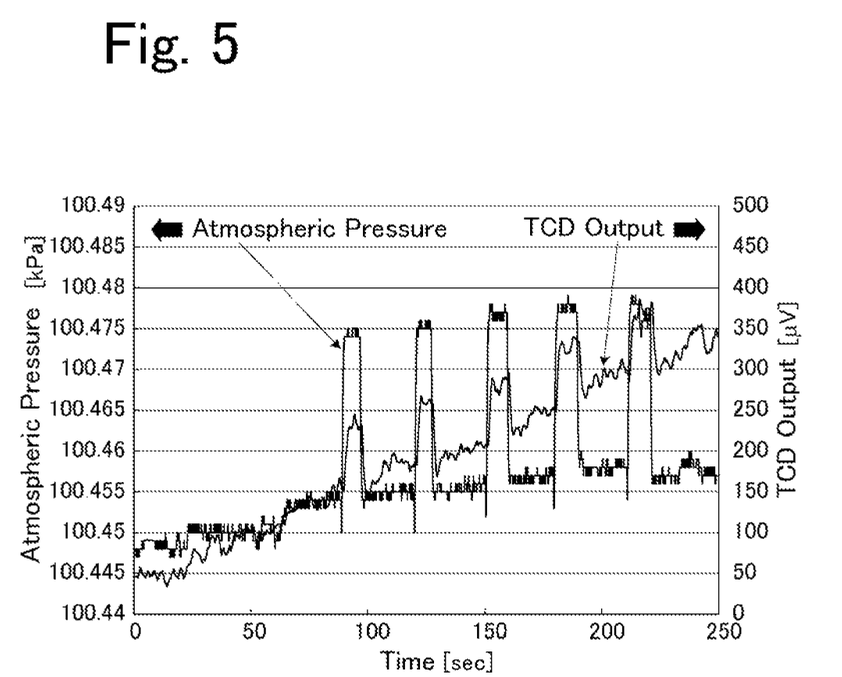
FIG. 5 is a diagram for describing a change in a baseline occurring at a time of occurrence of a change in the atmospheric pressure at a conventional thermal conductivity detector.

FIG. 5 is a diagram for describing a change in a baseline occurring, at a conventional thermal conductivity detector, at a time of occurrence of a change in the atmospheric pressure. In FIG. 5, the horizontal axis is time (unit s (second)), the vertical axis on the left is the atmospheric pressure (unit kPa (kilopascal)), and the vertical axis on the right is a TCD output (unit μV (micro volt)).

The conventional thermal conductivity detector is not provided with the buffer 5 and the resistance tube 7 (see FIG. 1). A change in the baseline (TCD output) shown in FIG. 5 coincides with the timing of a change in the atmospheric pressure. Accordingly, it can be seen that this change is based on the change in the atmospheric pressure.

As shown in FIG. 1, in the case where the buffer 5 of a volume V and the resistance tube 7 of a resistance R are attached at tip ends of the tubes 15*a* and 15*b*, the outlet pressures of the tubes 15*a* and 15*b* are given by Expression (1).

$$P_{vent} = P_{atm} + \Delta P_{atm} \times \exp\left(-\frac{t}{\tau}\right) \quad (1)$$

Here, $P_{Vent}$ is the outlet pressure (Pa) of the tube 15*a* or 15*b*, $P_{atm}$ is the atmospheric pressure (Pa), $\Delta P_{atm}$ is a change in the atmospheric pressure (Pa), and t is the time period of a change in the atmospheric pressure (sec).

τ is a time constant, and is indicated by Expression (2).

$$\tau = R \cdot C = R[\text{Pa} \cdot \text{sec/m}^3] \cdot \frac{V[\text{m}^3]}{\Delta P_{Vent}[\text{Pa}]} \quad (2)$$

Here, R is the resistance value (Pa·sec/m³) of the resistance tube 7, V is the volume (m³) of the buffer 5, and $\Delta P_{Vent}$ is a change in the outlet pressure (Pa) of the tube 15*a* or 15*b*.

In an experiment where the buffer 5 and the resistance tube 7 are not attached, it is known that if a change in the atmospheric pressure is at or lower than 7 (Pa), for example, a change in the baseline based on the change in the atmospheric pressure is not caused. Accordingly, a change in the baseline is not caused if $P_{Vent}$ does not reach 7 (Pa) in a case where the buffer 5 and the resistance tube 7 are attached.

In order for $P_{Vent}$ to not reach 7 (Pa), Expression (3) is to be satisfied.

$$7[\text{Pa}] > \Delta P_{atm}[\text{Pa}] \times \exp\left(-\frac{t[\text{sec}]}{R \cdot \frac{V}{7[\text{Pa}]}}\right) \quad (3)$$

The value of a change in the atmospheric pressure $\Delta_{P_{atm}}$, and the time period t of the change in the atmospheric pressure τ may be substituted in Expression (3) and the volume V and the value of the resistance R that satisfy Expression (3) are determined, and attachment to the tip ends of the tubes 15*a* and 15*b* is performed.

Figure 6:
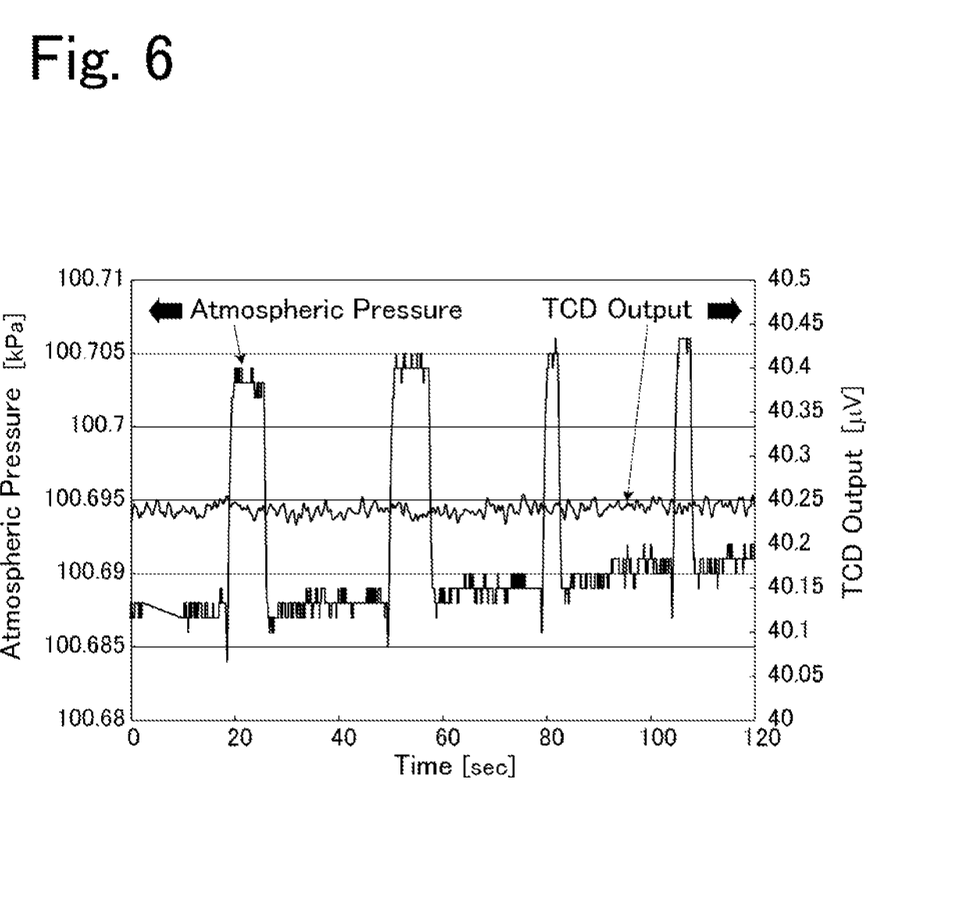
FIG. 6 is a diagram showing an output of an embodiment of the thermal conductivity detector and a change in an atmospheric pressure.

The baseline of the thermal conductivity detector 1 when the buffer 5 having a volume V of 2.25 (L (liter)) and the resistance tube 7 having a resistance R of 0.1 (Pa·sec/m³) are attached to the tubes 15*a* and 15*b* is shown in FIG. 6.

FIG. 6 is a diagram showing an output of an embodiment of the thermal conductivity detector and a change in the atmospheric pressure. In FIG. 6, the horizontal axis is time (unit sec), the vertical axis on the left is the atmospheric pressure (unit kPa), and the vertical axis on the right is a TCD output (unit μV).

Compared to the TCD output in FIG. 5, with the TCD output of the thermal conductivity detector 1 provided with the buffer 5 and the resistance tube 7, the baseline (the TCD output) is not changed even when there is a change in the atmospheric pressure. That is, it can be seen that the thermal conductivity detector 1 is able to remove a change in the baseline that is based on a change in the atmospheric pressure.

Figure 7:
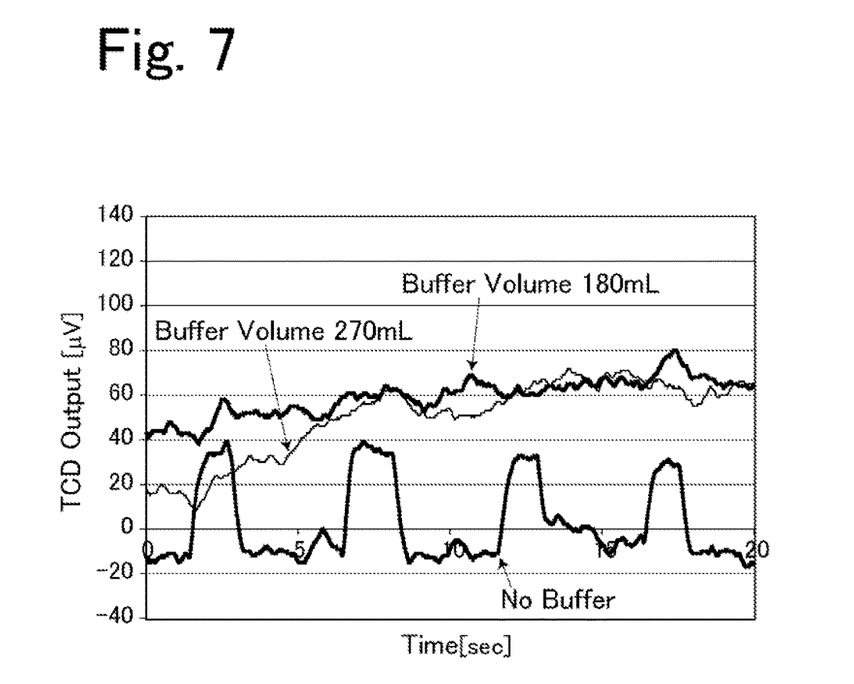
FIG. 7 is a diagram showing a result of studying output of an embodiment of the thermal conductivity detector with respect to a plurality of buffer volumes.

FIG. 7 is a diagram showing a result of studying output of an embodiment of the thermal conductivity detector with respect to a plurality of buffer volumes. In FIG. 7, the horizontal axis is time (unit sec), and the vertical axis is a TCD output (unit: μV). In FIG. 7, an output of the conventional thermal conductivity detector (without the buffer) is also shown as a reference.

It can be seen that a change in the baseline that is based on a change in the atmospheric pressure may be removed even when the volume of the buffer space 17 is smaller (180 mL 270 mL (milliliter)) than that in FIG. 6 (2.25 liters).

The thermal conductivity detector of the embodiment of the present invention may also be applied to a thermal conductivity detector where sample gas and reference gas are alternately introduced into a set of a temperature sensing element and a cell space. An example of the thermal conductivity detector of such an embodiment is shown in FIG. 8.

Figure 8:
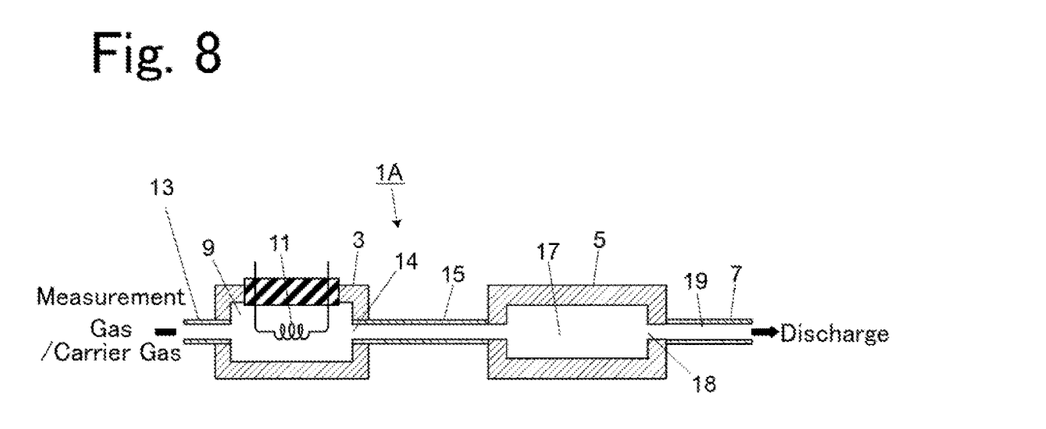
FIG. 8 is a schematic cross-sectional diagram showing another embodiment of the thermal conductivity detector.

According to a thermal conductivity detector 1A of an embodiment in FIG. 8, one cell space 9 is formed in a metal block 3, and a filament 11 is accommodated in the cell space 9. One end portion of each of metal tubes 13 and 15 is fitted and connected to the cell space 9. The other end portion of the tube 15, that is, the end portion on the opposite side from the metal block 3, is connected to a buffer 5 by, for example, a connector (not shown). One end of a resistance tube 7 is connected to the buffer 5 by, for example, a connector (not shown). The resistance tube 7 is connected to the buffer 5, on the opposite side from the tube 15.

Measurement gas and carrier gas are switched and introduced into the cell space 9 from the tube 13, and gas from the cell space 9 is discharged outside from the tube 15, through the buffer 5 and the resistance tube 7.

Figure 9:
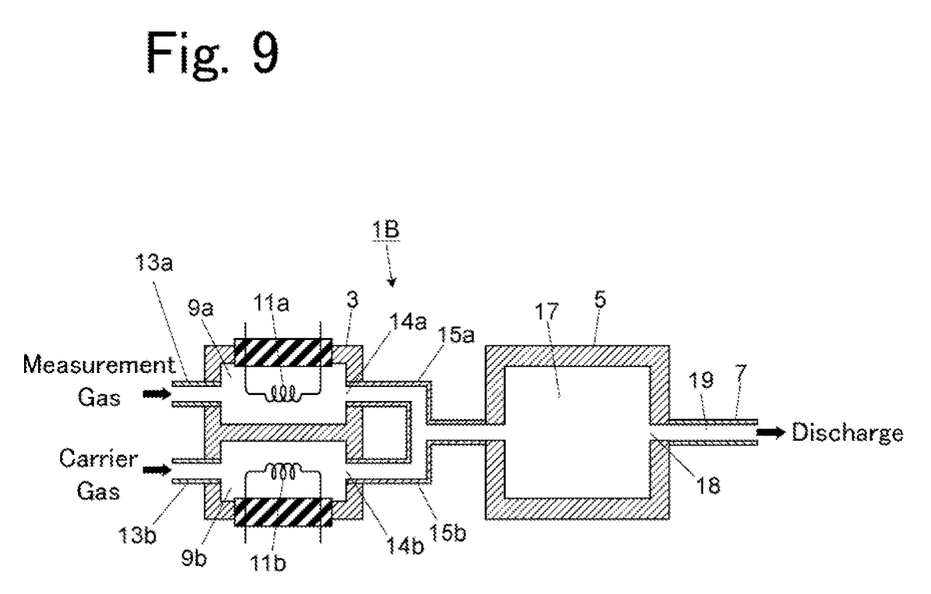
FIG. 9 is a schematic cross-sectional diagram showing further another embodiment of the thermal conductivity detector.

Also, in the embodiment in FIG. 1, the tubes 15*a* and 15*b* may be connected to the buffer space 17 after being joined together. FIG. 9 shows a thermal conductivity detector 1B of such an embodiment.

Heretofore, embodiments of the present invention have been described, but the configurations, arrangements, numerical values, materials and the like of the embodiments are only exemplary, and the present invention is not limited thereto, and various changes may be made within the scope of the present invention described in the claims.

The buffer 5 does not have to be a buffer tank, and it may be any container having a desired volume V, for example.

The resistance tube 7 does not have to be a resistance tube as long as it has a desired resistance R.

Also, the buffer 5 and the resistance tube 7 do not have to be attached to tip ends of the tubes 15, 15*a*, and 15*b*, and the buffer 5 (the buffer space 17) and the resistance tube 7 (the discharge channel 19) may be embedded in the metal block 3 to obtain one part.

Furthermore, the cell spaces 9, 9*a*, and 9*b* do not have to be formed by the metal block 3, and may be fabricated by, for example, an MEMS (Micro Electro Mechanical Systems) process. A small thermal conductivity detector may thereby be realized. The buffer space 17 and the discharge channel 19 may be embedded in a block for forming the cell space 9, 9*a* or 9*b* fabricated by the MEMS process.

What is claimed is:
1. A thermal conductivity detector comprising:
   a cell member provided with a cell space including a fluid inlet and a fluid outlet, wherein the fluid inlet is provided at one end of the cell space and the fluid outlet is provided at another end of the cell space;

a temperature sensing element, accommodated inside the cell space, whose electrical resistance is changed according to thermal conductivity of a fluid flowing through the cell space;

a detection circuit for detecting a change in the electrical resistance of the temperature sensing element;

a buffer space connected to and downstream of the fluid outlet of the cell space and having a cross-sectional area that is greater than a cross-sectional area of the fluid outlet, wherein fluid that has flowed through the cell space flows in the buffer space; and a discharge channel connected to a fluid outlet of the buffer space and having a cross-sectional area that is smaller than the cross-sectional area of the buffer space, wherein the cell space is formed from a sample-side cell space and a reference-side cell space that are separated from each other, each of the sample-side cell space and the reference-side cell space including a fluid inlet and a fluid outlet, wherein the temperature sensing element is formed from a temperature sensing element that is accommodated in the sample-side cell space and a temperature sensing element that is accommodated in the reference-side cell space, and wherein the connection tube is formed from two connection tubes of a sample-side connection tube connecting the sample-side cell space and the buffer space and a reference-side connection tube connecting the reference-side cell space and the buffer space.

2. A thermal conductivity detector comprising:

a cell member provided with a cell space including a fluid inlet and a fluid outlet, wherein the fluid inlet is provided at one end of the cell space and the fluid outlet is provided at another end of the cell space;

a temperature sensing element, accommodated inside the cell space, whose electrical resistance is changed according to thermal conductivity of a fluid flowing through the cell space;

a detection circuit for detecting a change in the electrical resistance of the temperature sensing element;

a buffer space connected to and downstream of the fluid outlet of the cell space and having a cross-sectional area that is greater than a cross-sectional area of the fluid outlet, wherein fluid that has flowed through the cell space flows in the buffer space; and a discharge channel connected to a fluid outlet of the buffer space and having a cross-sectional area that is smaller than the cross-sectional area of the buffer space, wherein the cell space is formed from a sample-side cell space and a reference-side cell space that are separated from each other, each of the sample-side cell space and the reference-side cell space including a fluid inlet and a fluid outlet, wherein the temperature sensing element is formed from a temperature sensing element that is accommodated in the sample-side cell space and a temperature sensing element that is accommodated in the reference-side cell space, and wherein the connection tube is formed from a sample-side connection tube connected to the fluid outlet of the sample-side cell space and a reference-side connection tube connected to the fluid outlet of the reference-side cell space, the connection tubes being connected to the buffer space as one connection tube.

3. A gas chromatograph for supplying carrier gas to a column through a sample introduction section, and detecting, by a thermal conductivity detector, a gas component that has been separated by and that has flowed out from the column, wherein the thermal conductivity detector comprises:

a cell member provided with a cell space including a fluid inlet and a fluid outlet, wherein the fluid inlet is provided at one end of the cell space and the fluid outlet is provided at another end of the cell space;

a temperature sensing element, accommodated inside the cell space, whose electrical resistance is changed according to thermal conductivity of a fluid flowing through the cell space;

a detection circuit for detecting a change in the electrical resistance of the temperature sensing element;

a buffer space connected to and downstream of the fluid outlet of the cell space and having a cross-sectional area that is greater than a cross-sectional area of the fluid outlet, wherein fluid that has flowed through the cell space flows in the buffer space; and a discharge channel connected to a fluid outlet of the buffer space and having a cross-sectional area that is smaller than the cross-sectional area of the buffer space, wherein the cell space is formed from a sample-side cell space and a reference-side cell space that are separated from each other, each of the sample-side cell space and the reference-side cell space including a fluid inlet and a fluid outlet, wherein the temperature sensing element is formed from a temperature sensing element that is accommodated in the sample-side cell space and a temperature sensing element that is accommodated in the reference-side cell space, and wherein the connection tube is formed from two connection tubes of a sample-side connection tube connecting the sample-side cell space and the buffer space and a reference-side connection tube connecting the reference-side cell space and the buffer space.

4. A gas chromatograph for supplying carrier gas to a column through a sample introduction section, and detecting, by a thermal conductivity detector, a gas component that has been separated by and that has flowed out from the column, wherein the thermal conductivity detector comprises:

a cell member provided with a cell space including a fluid inlet and a fluid outlet, wherein the fluid inlet is provided at one end of the cell space and the fluid outlet is provided at another end of the cell space;

a temperature sensing element, accommodated inside the cell space, whose electrical resistance is changed according to thermal conductivity of a fluid flowing through the cell space;

a detection circuit for detecting a change in the electrical resistance of the temperature sensing element;

a buffer space connected to and downstream of the fluid outlet of the cell space and having a cross-sectional area that is greater than a cross-sectional area of the fluid outlet, wherein fluid that has flowed through the cell space flows in the buffer space; and a discharge channel connected to a fluid outlet of the buffer space and having a cross-sectional area that is smaller than the cross-sectional area of the buffer space, wherein the cell space is formed from a sample-side cell space and a reference-side cell space that are separated from each other, each of the sample-side cell space and the reference-side cell space including a fluid inlet and a fluid outlet, wherein the temperature sensing element is formed from a temperature sensing element that is accommodated in the sample-side cell space and a temperature sensing element that is accommodated in the reference-side cell space, and wherein the connection tube is formed from a sample-side connection tube connected to the fluid outlet of the sample-side cell space and a reference-side connection tube connected to the fluid outlet of the reference-side cell space, the connection tubes being connected to the buffer space as one connection tube.

* * * * *